United States Patent [19]
Lim et al.

[11] Patent Number: 5,594,131
[45] Date of Patent: Jan. 14, 1997

[54] PROCESS FOR PREPARING CEPHALOSPORIN INTERMEDIATES

[75] Inventors: Gary M. F. Lim, Fayetteville; John M. Roubie, East Syracuse, both of N.Y.

[73] Assignee: Bristol-Myers Squibb COmpany, New York, N.Y.

[21] Appl. No.: 382,556

[22] Filed: Feb. 2, 1995

Related U.S. Application Data

[63] Continuation of Ser. No. 252,814, Jun. 2, 1994, abandoned, which is a continuation of Ser. No. 110,468, Aug. 23, 1993, abandoned, which is a continuation of Ser. No. 920,232, Jul. 24, 1992, abandoned.

[51] Int. Cl.$^6$ .................. C07D 501/46; C07D 501/24
[52] U.S. Cl. .................................. 540/222; 540/219
[58] Field of Search ............................. 540/222

[56] References Cited

U.S. PATENT DOCUMENTS

| | | |
|---|---|---|
| 4,406,899 | 9/1983 | Aburaki et al. |
| 4,659,812 | 4/1987 | Aburaki et al. |
| 4,714,760 | 12/1987 | Brundidge et al. |
| 4,868,294 | 9/1989 | Brundidge et al. |
| 4,910,301 | 3/1990 | Kaplan et al. |

OTHER PUBLICATIONS

Walker, et al, *J. of Organic Chemistry*, vol. 53, 1988, pp. 983–991.
Chemical Engineering News, Jul. 9, 1990, pp. 6–7.
Chemical Engineering News, Sep. 9, 1991, pp. 27–28.
The Wall Street Journal, Feb. 12, 1992.
Chemical & Engineering News, Jun. 22, 1992, pp. 7–13.

*Primary Examiner*—Mukund J. Shah
*Assistant Examiner*—Pavanaram K. Sripada
*Attorney, Agent, or Firm*—Aldo A. Algieri

[57] ABSTRACT

The present invention provides a process for the preparation of stable, crystalline cephalosporin intermediates of the formula

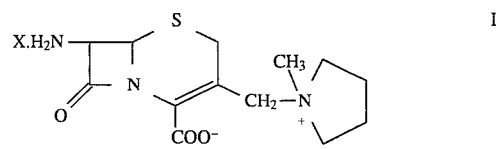

wherein X is HI, HCl or $H_2SO_4$ which are substantially free of the $\Delta^2$ isomer, and which are convertible into broad-spectrum cephalosporin antibiotics.

10 Claims, No Drawings

PROCESS FOR PREPARING CEPHALOSPORIN INTERMEDIATES

This is a continuation of application U.S. Ser. No. 08/252,814 filed Jun. 2, 1994 now abandoned, which is a continuation of U.S. Ser. No. 08/110,468 filed Aug. 23, 1993 now abandoned, which is a continuation of U.S. Ser. No. 07/920,232 filed Jul. 24, 1992, now abandoned.

BACKGROUND OF THE INVENTION

1. Field of the Invention

The present invention provides a process for the preparation of stable, crystalline salts of a cephalosporin intermediate which are substantially free of the $\Delta^2$ isomer and are convertible into broad-spectrum cephalosporin antibiotics.

2. Background Art

A large number of cephalosporin antibiotics are known and are widely used in the treatment of bacterial infection. The semi-synthetic antibiotic cefepime is a useful broad-spectrum antibiotic which is described by Aburaki, et al, in U.S. Pat. No. 4,406,899, issued Sep. 27, 1983 and by Kaplan, et al, in U.S. Pat. No. 4,910,301, issued Mar. 20, 1990 which is represented by the formula

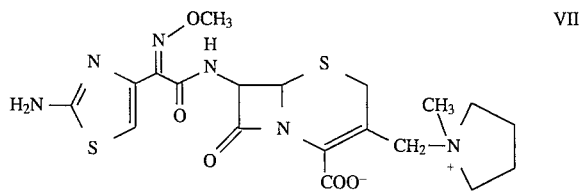

A preferred process for the preparation of the antibiotic cefepime comprises the 7-acylation of a stable, crystalline compound of the formula

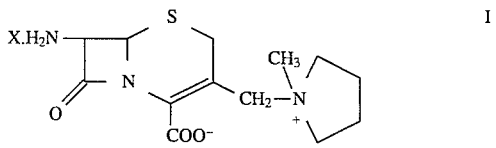

wherein X is HI, HCl or $H_2SO_4$ and which are substantially free of the $\Delta^2$ isomer. These crystalline cephalosporin intermediates are disclosed by Brundidge, et al, in U.S. Pat. No. 4,714,760, issued Dec. 22, 1987 and by Aburaki, et al, in U.S. Pat. No. 4,659,812, issued Apr. 21, 1987.

In U.S. Pat. No. 4,868,294, issued Sep. 19, 1989, Brundidge et al. describe the preparation of stable, crystalline 7-amino-3-[(1-methyl-1-pyrrolidinio)methyl] ceph-3-em-4-carboxylate salts substantially free of the $\Delta^2$ isomer starting from 7-amino cephalosporanic acid (7-ACA) in 1,1,2-trichlorotrifluoroethane (Freon TF) or 1,1,1-trichlorotrifluoroethane as the solvent.

However, by international agreement under the Montreal Protocol on Substances That Deplete the Ozone Layer and the subsequent 1990 London amendment, the international community agreed to curb and ban the production of chlorofluorocarbons (CFCs) by the end of the century. Recently, under terms of the 1990 Clean Air Act, the United States has moved up the deadline to cease production of CFCs and other ozone-depleting chemicals, including Freon TF, to the end of 1995.

The preparation of intermediates of Formula I substantially free of the $\Delta^2$ isomer is advantageously carried out as described in U.S. Pat. No. 4,868,294 in Freon TF as the solvent. By international agreement and United States law, the production of Freon TF will be phased out and Freon TF will be banned from commercial use. Thus, there is an urgent need to find a suitable solvent replacement for Freon TF in the preparation of intermediates of Formula I. The replacement solvent must meet certain criteria such as solubility of reactants, reaction rates, ratios of reactants, high yields and, more importantly, the elimination of the undesirable $\Delta^2$ isomer. Consequently the criteria for the process to produce the intermediates of Formula I severely restricts the selection of a solvent. The unique characteristics of Freon TF and, its isomer, as the solvent in the process for the preparation of intermediates of the Formula I are described by D. Walker et al. in the *Journal of Organic Chemistry*, Vol. 53, 1988, pages 983–991. On page 985, D. Walker et al. state that Freon TF and, its isomer, were the only two solvents which provided the best yields while minimizing in situ formation of the undesirable $\Delta^2$ isomer. In view of the teachings of the art, it was unexpected and surprising that the present inventors discovered that a series of cycloalkanes would substitute for the chlorofluorocarbons, Freon TF and its isomer, in the process for the preparation of intermediates of the Formula I starting from 7-ACA.

SUMMARY OF THE INVENTION

This invention relates to a process for the preparation of stable, crystalline salts of a cephalosporin intermediate having the formula

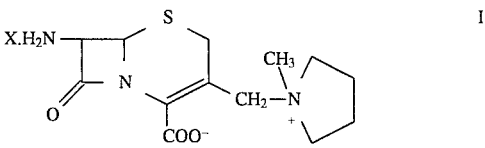

wherein X is HI, HCl or $H_2SO_4$, which are substantially free of the $\Delta^2$ isomer, and which are convertible into broad-spectrum cephalosporin antibiotics without the necessity of blocking or deblocking steps. This invention also relates to methods for making salts of Formula I, and intermediates in the preparation of the salts of Formula I in a $C_{5-8}$ cycloalkane optionally substituted by one or two (lower)alkyl.

DETAILED DESCRIPTION OF THE INVENTION

The present invention provides a process for the preparation of compounds of Formula I

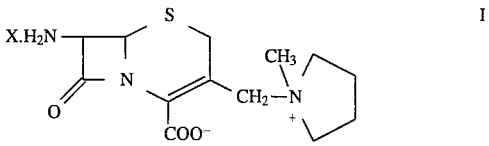

wherein X is HI, HCl or $H_2SO_4$. When the compounds of Formula I are prepared as described by the instant process, they are crystalline, temperature stable and substantially free of the corresponding $\Delta^2$ isomer. As a result of being substantially free of the $\Delta^2$ isomer, the compounds of Formula I are convertible (by acylation) to broad spectrum cephalosporins which themselves are substantially free of the $\Delta^2$ isomer, without the need for chromatographic separation of the $\Delta^2$ and $\Delta^3$ isomers. As a result of their temperature stability, they may be isolated and stored, and converted to the end products when desired. Also, the intermediates of Formula I do not require blocking (protection) of the carboxyl group prior to acylation or deblocking (deprotection) of the carboxyl group after acylation, thus offering process efficiency. However, an additional major advantage of the instant process is that it does not use chlorofluorocarbons (CFCs) as the organic solvent but rather cycloalkanes which are not known to deplete the ozone layer of the earth's upper atmosphere.

The compounds of Formula I may be prepared by treating a solution of the compound of the formula

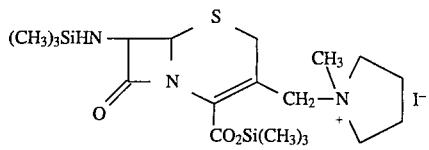

in a $C_{5-8}$ cycloalkane optionally substituted by one or two (lower)alkyl with a (lower)alkanol or water to remove the trimethylsilyl groups, followed by HI, HCl or $H_2SO_4$ to produce the hydriodide, hydrochloride or sulfate salt, respectively. It is preferred to use a (lower)alkanol for removal of the trimethylsilyl groups, and most preferably methanol or 2-propanol. The reaction is conducted at a temperature of from about $-10°$ C. to about 25° C., and preferably at a temperature of from about 0° C. to about 10° C. From about 1 to about 5 equivalents of 2-propanol are used per equivalent of Compound II, and preferably, from about 1 to about 3 equivalents of 2-propanol.

The compound of Formula II may be prepared by reacting a solution of the compound of the formula

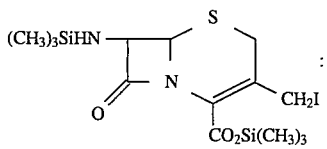

in a $C_{5-8}$ cycloalkane optionally substituted by one or two (lower)alkyl with N-methylpyrrolidine (NMP). It has surprisingly been found that the use of a $C_{5-8}$ cycloalkane optionally substituted by one or two (lower)alkyl as solvent produces Compound II which is substantially free of the $\Delta^2$ isomer, while commonly used solvents such as methylene chloride, carbon tetrachloride, chloroform or dioxane produce Compound II which contains large amounts of the undesirable $\Delta^2$ isomer (e.g. 50% $\Delta^2$ isomer).

The reaction is conducted at a temperature of from about $-10°$ C. to about 40° C., and preferably from about 10° C. to about 30° C. Although it is possible to use greater or lesser amounts of N-methylpyrrolidine, we obtain highest purity of product when about 1 to 1.5 equivalents of NMP is utilized per equivalent of Compound III.

The compounds of Formula III may be prepared by reacting a solution of the compound of the formula

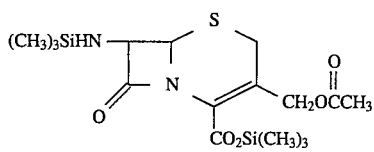

in a $C_{5-8}$ cycloalkane optionally substituted by one or two (lower)alkyl with trimethylsilyl iodide (TMSI). Surprisingly, these solvents yield Compound III which is substantially free of the $\Delta^2$ isomer, while common solvents such as chlorobenzene, dioxane, carbon tetrachloride, 1,2-dichloroethane and the like, give significant amounts of the undesirable $\Delta^2$ isomer.

The reaction is conducted at a temperature of from about 5° C. to about 45° C., but preferably is conducted at ambient temperature for convenience. At least one equivalent of TMSI is required to convert all of Compound IV to Compound III. We prefer to utilize an amount of from about 0.9 to about 1.5 equivalents per equivalent of Compound IV. More preferable, we utilize from about 1.0 to about 1.2 equivalents of TMSI.

The compounds of Formula IV may be prepared by reacting 7-aminocephalosporanic acid (7-ACA), i.e., the compound of the formula

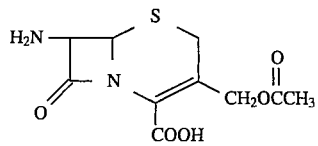

with hexamethyldisilazane (HMDS) in the presence of about 0.01 to about 0.1 equivalents of TMSI per equivalent of 7-ACA, in a $C_{5-8}$ cycloalkane optionally substituted by one or two (lower)alkyl at a temperature from room temperature to the boiling point of the solvent. Preferably, the reaction is conducted at about 50° C. to about 55° C. The HMDS may be used in an amount of from about 0.95 to about 1.4 equivalents per equivalent of 7-ACA, and preferably from about 1.0 to about 1.3 equivalents of HMDS per equivalent of 7-ACA. We most prefer to utilize 1.2 equivalents of HMDS.

In a preferred process for the preparation of Compound II, a solution of Compound IV in a $C_{5-8}$ cycloalkane optionally substituted by one or two (lower)alkyl is first treated with N-methylpyrroldine followed by the addition of at least one equivalent of TMSI. The reaction can be conducted at a temperature of from about 5° C. to about 45° C. For convenience, we prefer to conduct the reaction at about 35° C. The N-methylpyrrolidine may be used in an amount of from about 1.0 to about 2.0 equivalents per equivalent of Compound IV, and preferably from about 1.2 to about 1.5 equivalents. The TMSI may be used in an amount of from about 1.0 to about 3.0 equivalents per equivalent of Compound IV, and preferably from about 1.5 to 2.0 equivalents.

In the most preferred process for the preparation of Compound II, a solution of Compound IV in a $C_{5-8}$ cycloalkane optionally substituted by one or two (lower)alkyl is reacted with N-methyl-N-trimethylsilylpyrroldinio iodide having the formula

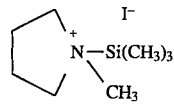

at a temperature of from about 5° C. to about 45° C. For convenience, we prefer to conduct the reaction at about 35° C. The compound of Formula VI may be used in an amount of from about 1.0 to about 2.0 equivalents per equivalent of Compound IV, and preferably from about 1.2 to about 1.5 equivalents of Compound VI per equivalent of Compound IV. If desired, a small amount of imidazole (e.g. 0.1 equivalents) may be added to the reaction mixture to shorten the reaction time. We have found that, when preparing Compound II by the reaction of Compound IV with Compound VI, it is advantageous to add a small amount of TMSI of about 0.1 to 0.5 equivalents, and preferably, about 0.4 equivalents per equivalent of Compound V.

The compound of Formula VI may be prepared by reacting N-methylpyrrolidine with about an equimolar amount of TMSI in $C_{5-8}$ cycloalkane optionally substituted by one or two (lower)alkyl as solvent, at a temperature of from about $-10°$ C. to about 25° C. We prefer to conduct the reaction at a temperature of from about 10° C. to about 20° C. The reaction ratio of NMP and TMSI may be varied, but we obtain excellent results by utilizing equimolar amounts.

In the most preferred process, the compounds of Formula I are prepared from 7-ACA in a "one pot" reaction, i.e. without the isolation of any intermediates. Accordingly, when conducting the "one pot" reaction, the reaction is preferably conducted in a $C_{5-8}$ cycloalkane optionally substituted by one or two (lower)alkyl, as described herein.

As used herein and in the claims, the term "(lower)alkyl" means a straight or branched chain alkyl group containing from 1 to 4 carbon atoms such as methyl, ethyl, propyl, isopropyl, butyl, isobutyl and t-butyl. Preferably, (lower)alkyl contains 1 to 2 carbon atoms. The term "(lower)alkanol" as used herein and in the claims means a straight or branched chain alkoxy group, preferably, containing from 1 to 6 carbon atoms such as methyl, ethyl, propyl, isopropyl, butyl, isobutyl, t-butyl, amyl, hexyl, and the like. The term "$C_{5-8}$ cycloalkane optionally substituted by one or two (lower)alkyl" as used herein and in the claims means a carbon cyclic ring system such as cyclopentane, cyclohexane, cycloheptane, cyclooctane, methylcyclopentane, methylcyclohexane, ethylcyclohexane, isopropylcyclohexane, propylcyclohexane, butylcyclohexane, tert-butylcyclohexane, 1,3-dimethylcyclohexane, 1,4-dimethylcyclohexane and the like.

The compounds of Formula I are readily converted to broad spectrum antibiotics by acylation with the appropriate side-chain acid. For example, a compound of Formula I (X=HI, HCl or $H_2SO_4$) is converted to 7-[α-(2-aminothiazol-4-yl)-α-(Z)methoxyiminoacetamido]-3-[(1-methyl-1-pyrrolidinio)methyl]-3-cephem-4-carboxylate (VIII) by N-acylating with 1-benzotriazolyl (Z)-2-(2-aminothiazol-4-yl)-2-methoxyiminoacetate ester. The reaction equation is set forth below.

ester is a known compound and is described in Hoechst, Japan Kokai 54-95593 (7/28/79) and German application No. 2758000.3 (12/24/77). The utility of the compound (VIII) is shown in Abruaki et al, U.S. Pat. No. 4,406,899.

DESCRIPTION OF SPECIFIC EMBODIMENTS

EXAMPLE 1

(6R,7R)-7-Amino-3-[(1-methyl-1-pyrrolidinio)methyl] ceph-3-em-4-carboxylate hydriodic salt To a suspension of 7-ACA (20.0g, 73.5 mmol) in anhydrous cyclohexane (140 ml) at 20°–25° C. was added hexamethyldisilazane (HMDS, 18.6 ml, 88.0 mmol) followed by iodotrimethylsilane (TMSI, 0.4 ml, 2.8 mmol). The resulting suspension was heated to reflux in vacuo at a pot temperature of about 55° C. and maintained for 12 hours to produce a thin slurry of silylated 7-ACA. The slurry is then cooled to about 15°–20° C.

To a separate solution of N-methylpyrrolidine (NMP, 10.68 ml, 102.7 mmol) in anhydrous cyclohexane (40 ml) was added iodotrimethylsilane (TMSI, 14.6 ml, 102.7 mmol) dropwise at 15°–20° C. The thick slurry containing TMSI/NMP was agitated for 10 minutes at 15°–20° C.

The silylated 7-ACA slurry was added to the TMSI/NMP slurry and the mixture was agitated for 30 minutes at 15°–20° C. Next, iodotrimethylsilane (TMSI, 4.2 ml, 29.5 mmol) was added and the reaction mixture was warmed to about 37° C. for 40 hours under a slight stream of nitrogen. The thick product slurry was then cooled to about 5° C. and 2-propanol (10 ml) was added dropwise keeping the temperature at or below 10° C. After agitating the mixture for 15 minutes with continued cooling, a solution of hydriodic acid (20 ml of 57% HI in 30 ml of water) was added. The

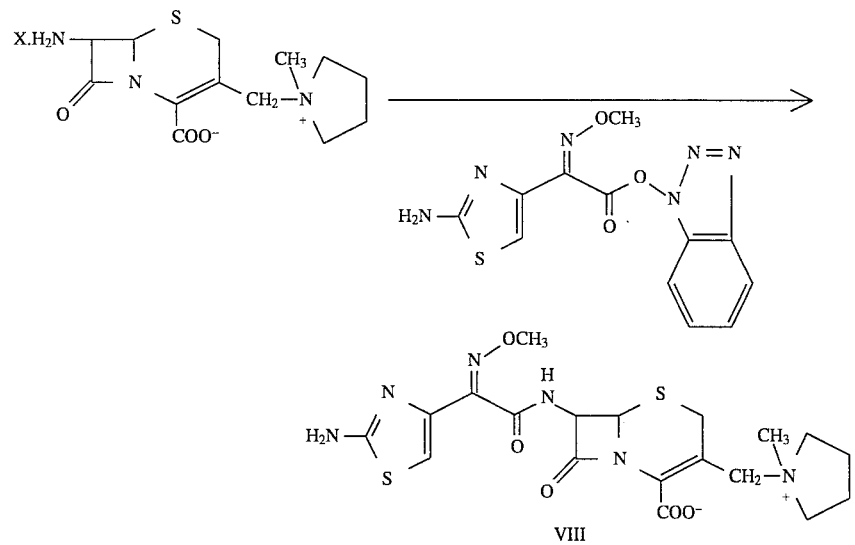

VIII

This reaction is readily carried out in the presence to N,N-dimethylaniline in dimethylformamide at room temperature over a period of 10–20 hours; or by dissolving (I) in water and dimethylformamide and adding sodium bicarbonate with ice cooling, and reacting at room temperature for about 30 minutes to about 5 hours; or by dissolving (I) in water, cooling to 5°–15° C., adding NaOH dropwise to pH 5.5–6, adding tetrahydrofuran, adding sodium hydroxide to adjust the pH to 6.7–6.9, adding the active ester reactant and reacting for 1 to 5 hours at room temperature. The active temperature was allowed to rise to 20° C. and the two-liquid phase mixture was agitated for 15 minutes at about 20° C. The rich aqueous phase was separated and the spent cyclohexane phase was washed with water (10 ml). The combined aqueous extract was treated with diatomaceous earth (3 g), agitated for 5 minutes at 20°–25° C. then treated with decolorizing carbon (4 g). After agitating for 30 minutes at 20°–25° C., the mixture was filtered and the spent cake was washed with water (40 ml). The filtrate was diluted with 2-propanol (500 ml) to crystallize the product. The resulting product slurry was cooled to 0°–5° C. and was agitated for 1 hour. The slurry was filtered and washed with 80 ml of 2-propanol:water (4:1) and 80 ml of 2-propanol. Further drying in vacuo at 45° C. afforded 18.5 g (59.2%) of crystalline (6R, 7R)-7-amino-3-[(1-methyl-1-pyrrolidinio)methyl]ceph-3-em-4-carboxylate monohydriodide. Purity as determined by HPLC was 97.3%. The $^1$H NMR spectrum observed with the title compound is the same as an authentic sample prepared by the method in the art using Freon TF (U.S. Pat. No. 4,714,760): $^1$H NMR (D$_2$O, 360 MHz) δ: 2.14–2.32 (envelope, 4H, —N(CH$_3$)CH$_2$CH$_2$—), 3.00 (s, 3H, NCH$_3$), 3.46–3.67 (m, 5H, —N(CH$_3$)CH$_2$CH$_2$; SCH$_2$), 3.96 (d, 1H, J=16.9 Hz, —SCH$_2$), 4.09 (d, 1H, J=13.9 Hz, =CCH$_2$N—), 4.73 (d, 1H, J=13.9 Hz, =CCH$_2$N—), 5.21 (d, 1H, J=5.1 Hz, —COCHCHS—), 5.41 (d, 1H, J=5.1 Hz, —COCHCHS).

EXAMPLE 2

7-Amino-3-[(1-methyl-1-pyrrolidinio)methyl] ceph-3-em-4-carboxylate hydriodic salt To a suspension of 7-ACA (20g, 73.5 mmol) in anhydrous cyclohexane (140 ml, containing an anti-static agent) was added 18.6 ml (88.0 mmol) of hexamethyldisilazane and 0.4 ml (2.8 mmol) of iodotrimethylsilane at 20°–25° C. The resulting suspension was heated to reflux in vacuo at a pot temperature of about 50° C. and maintained for 10 hours. The thin suspension was then agitated for 14 hours at 50° C. at atmospheric pressure with a slight nitrogen purge and further cooled to 20° C. and held for 6 hours.

To a separate solution of N-methylpyrrolidine (NMP, 10.68 ml, 102.7 mmol) in cyclohexane (40 ml, containing an anti-static agent) was added dropwise at 15°–20° C. 14.60 ml (102.7 mmol) of iodotrimethylsilane (TMSI). The suspension was stirred for 10 minutes at 15°–20° C.

The silylated 7-ACA slurry was added to the TMSI/NMP suspension and the mixture was agitated for 30 minutes at 15° C. To the mixture was added 4.2 ml (29.5 mmol) of iodotrimethylsilane. The suspension was heated at 35° C. with a nitrogen purge for 40 hours. The product suspension was cooled to 5° C. and 2-propanol (10 ml) was added dropwise at 5°–10° C. The suspension was agitated for 15 minutes in an ice-water bath. To the suspension was added, a solution of hydriodic acid (20 ml of 57% HI in 30 ml of water). The temperature was allowed to rise to 20° C. and the mixture was stirred for 15 minutes at 20° C. The rich aqueous layer was separated and combined with a water wash (10 ml) of the spent cyclohexane. To the combined aqueous phase was added diatomaceous earth (3 g) followed 5 minutes later by activated carbon (4 g). After carbon treatment for 30 minutes at 20°–25° C., the carbon was removed by filtration and the spent carbon cake was washed with water (40 ml). Dilution of the aqueous with 2-propanol (500 ml) gave a slurry of crystalline product. After 2 hours of agitation at 0°–5° C., the product was collected by filtration, washed with a 2-propanol:water (4:1) mixture (80 ml) and 2-propanol (80 ml). After drying at 45° C. in vacuo, the yield was 18.1 g (57.8%) of the title compound. Purity as determined by HPLC was 95.1%.

EXAMPLE 3

7-Amino-3-[(1-methyl-1-pyrrolidinio)methyl] ceph-3-em-4-carboxylate hydriodic salt To a suspension of 7-ACA (20g, 73.5 mmol) in anhydrous cyclohexane (140 ml) was added 18.6 ml (88.0 mmol) of hexamethyldisilazane and 0.4 ml (2.8 mmol) of iodotrimethylsilane. The resulting mixture was agitated for 21 hours at 50° C. with a slight nitrogen purge then cooled to 20° C. and held for 5.5 hours. Cyclohexane (50 ml) was added and the suspension was heated to distill off 50 ml of solvent (in vacuo) at a pot temperature of 42° C.

To a solution of N-methylpyrrolidine (NMP, 10.68 ml, 102.7 mmol) in cyclohexane (40 ml) was added dropwise at 15°–20° C., 14.6 ml (102.7 mmol) of iodotrimethylsilane (TMSI). The suspension was stirred at 15°–20° C. for 10 minutes.

The silylated 7-ACA slurry was added to the TMSI/NMP suspension and stirred for 30 minutes while cooling to 5° C. Iodotrimethylsilane (4.2 ml, 29.5 mmol) was added and the suspension was heated to 35° C. for 45 hours. After cooling the product suspension to 5° C., 2-propanol (10 ml) was added dropwise at a temperature of 5°–10° C. The suspension was stirred in an ice-bath for 15 minutes. Coolant was removed and a solution of 20 ml of 57% HI in water (30 ml) was added. The temperature was allowed to rise to 20° C. The mixture was stirred for 15 minutes at 20° C., then the aqueous phase was separated. A water (10 ml) wash of the cyclohexane layer was added to the rich aqueous and diatomaceous earth (3 g) was added. After 5 minutes agitation, activated carbon (4 g) was added and agitation continued for 30 minutes. The activated carbon was removed by filtration using a water wash (40 ml) on the spent carbon cake. The decolorized aqueous phase was diluted with 2-propanol (500 ml) to crystallize the product. After 1 hour of agitation at 0°–5° C., the product was collected by filtration, washed with 2-propanol:water (4:1) mixture (80 ml) and 2-propanol (80 ml) and dried at 45° C. in vacuo. Yield of the title compound was 14.89 g (47.7%). Purity as determined by HPLC was 97.4%.

EXAMPLE 4

7-Amino-3-[(1-methyl-1-pyrrolidinio)methyl] ceph-3-em-4-carboxylate hydriodic salt To a suspension of 7-ACA (20g, 73.5 mmol) in anhydrous cyclohexane (140 ml) was added 18.6 ml (88.0 mmol) of hexamethyldisilazane and 0.4 ml (2.8 mmol) of iodotrimethylsilane. With nitrogen purge, the suspension was heated to 81° C. and refluxed for 1 hour. The thin product suspension was cooled to 10° C. for 3 hours.

To a solution of N-methylpyrrolidine (NMP, 10.68 ml, 102.7 mmol) in cyclohexane (40 ml) was added dropwise at 15°–20° C., 14.60 ml (102.7 mmol) of iodotrimethylsilane (TMSI). The resulting slurry was agitated at 15°–17° C. for 15 minutes.

The silylated ACA slurry was added and the mixture was stirred for 30 minutes at 15°–17° C. Iodotrimethylsilane (4.2 ml, 29.5 mmol) was added and the suspension was heated to 40° C. in 80 minutes, then held at 40° C. for 23 hours under slight nitrogen purge.

The product suspension was cooled to 5° C. and 2-propanol (10 ml) was added dropwise at 5°–10° C. The suspension was agitated for 10 minutes in an ice-bath. To the suspension was added hydriodic acid (20 ml of 57% HI in 30 ml of water). The temperature was allowed to warm to 20° C. and the batch was agitated for 10 minutes. The rich aqueous was separated and combined with a 10 ml water extract of the spent cyclohexane phase. Diatomaceous earth (3 g) was added and after 5 minutes agitation, activated carbon (4 g) was added and agitation continued for 30 minutes. The carbon was removed by filtration and the spent cake was washed with water (40 ml). The rich aqueous was diluted with 2-propanol (500 ml) to crystallize the product. The product slurry was cooled to 0°–5° C., agitated 30 minutes, filtered and washed with 2-propanol:water (4:1) mixture (80 ml) and 2-propanol (80 ml). After drying at 45° C. in vacuo, the yield of the title compound was 8.42g (27%). Purity as determined by HPLC was 83.7%.

EXAMPLE 5

7-Amino-3-[(1-methyl-1-pyrrolidinio)methyl] ceph-3-em-4-carboxylate hydriodic salt To a suspension of 7-ACA (20g, 73.5 mmol) in cyclopentane (140 ml) was added 18.6 ml (88.0 mmol) hexamethyldisilazane and 0.4 ml (2.8 mmol) of iodotrimethylsilane. The suspension was heated to reflux at 49° C. with a slight nitrogen purge. Reflux was maintained for 24 hours. Cyclopentane (50 ml) was added and 50 ml of solvent was then distilled from the reactor. The thin slurry was cooled to 20° C. for 3 hours.

To a solution of N-methylpyrrolidine (NMP, 10.68 ml, 102.7 mmol) in cyclopentane (40 ml) was added dropwise at 10°–15° C., 14.6 ml (102.7 mmol) of iodotrimethylsilane (TMSI). The resulting slurry was cooled to 10° C. for 20 minutes and the silylated ACA was added. The slurry was agitated at 10°–15° C. for 30 minutes. After addition of 4.2 ml (29.5 mmol) iodotrimethylsilane the slurry was warmed to 35° C. and agitated under slight nitrogen pressure for 44 hours. The product slurry was cooled to 5° C. and 2-propanol (10 ml) was added dropwise at 5°–10° C. The slurry was agitated for 15 minutes at 5°–10° C. Hydriodic acid (20 ml of 57% HI in 30 ml of water) was added and the temperature was allowed to reach 20° C. The mixture was agitated for 15 minutes and rich aqueous phase separated. The spent cyclopentane layer was washed with water (10 ml). To the combined aqueous phase was added diatomaceous earth (3 g) and after 5 minutes at 20°–25° C., 4 g of activated carbon. Carbon treatment was continued for 30 minutes. The carbon was removed by filtration with a water (40 ml) wash of the spent carbon cake. The filtrate was diluted with 2-propanol (500 ml) to crystallize the product. The product slurry was cooled to 0°–5° C., agitated 1.5 hours, filtered and washed with 2-propanol:water (4:1) mixture (80 ml) then 2-propanol (80 ml). After drying at 45° C., the yield of the title compound was 17.47g (56%). Product purity determined by HPLC was 97.2%.

EXAMPLE 6

7-Amino-3-[(1-methyl-1-pyrrolidinio)methyl] ceph-3-em-4-carboxylate hydriodic salt To a suspension of 7-ACA (20g, 73.5 mmol) in cyclopentane (140 ml, containing an anti-static agent) was added 18.6 ml (88.0 mmol) of hexamethyldisilazane and 0.4 ml (2.8 mmol) of iodotrimethylsilane. The suspension was heated to reflux at 49° C. with a slight nitrogen purge. Reflux was maintained for 24 hours. The thin suspension was cooled to 20° C. for 4 hours.

To a solution of N-methylpyrrolidine (NMP, 10.68 ml, 102.7 mmol) in cyclopentane (40 ml) was added dropwise at 15°–20° C., 14.6 ml (102.7 mmol) of iodotrimethylsilane (TMSI). The resulting slurry was agitated for 10 minutes at 15° C. The silylated 7-ACA was added and the suspension was agitated at 15° C. for 30 minutes. Iodotrimethylsilane (4.2 ml, 29.5 mmol) was added and the mixture was agitated under slight nitrogen purge for 40 hours at 35° C.

The product mixture was cooled to 6° C. and 2-propanol (10 ml) was added dropwise at 6°–10° C. The mixture was agitated for 15 minutes. A solution of hydriodic acid (20 ml of 57% HI in 30 ml of water) was added and the temperature was allowed to reach 20° C. After 15 minutes agitation, the rich aqueous phase was separated. The spent cyclopentane phase was washed with water (10 ml). To the combined rich aqueous phase was added diatomaceous earth (3 g) and after 5 minutes agitation, activated carbon (4 g) was added. Carbon treatment was continued for 30 minutes at 20°–25° C. The carbon was removed by filtration with a water (40 ml) wash of the spent carbon cake. The filtrate was diluted with 2-propanol (500 ml) to crystallize the product. The product slurry was cooled to 0°–5° C. for 1.5 hours, filtered and washed with 2-propanol:water (4:1) mixture (80 ml) then 2-propanol (80 ml). After drying at 45° C. in vacuo, the yield of the title compound was 17.6 g (56.3%). Product purity as determined by HPLC was 97%.

EXAMPLE 7

7-Amino-3-[(1-methyl-1-pyrrolidinio)methyl] ceph-3-em-4-carboxylate hydriodic salt To a suspension of 7-ACA (20g, 73.5 mmol) in methylcyclohexane (140 ml) was added 18.6 ml (88.0 mmol) of hexamethyldisilazane and 0.4 ml (2.8 mmol) of iodotrimethylsilane. The suspension was heated to reflux in vacuo at 50° C. for 10 hours. The vacuum source was then replaced with a nitrogen purge and the reaction was agitated for an additional 12 hours. Methylcyclohexane (50 ml) was then added and 50 ml of solvent was distilled out in vacuo at 50° C. The silylation slurry was held at 20°–25° C. for 3 hours.

To a solution of N-methylpyrrolidine (NMP, 10.68 ml, 102.7 mmol) in methylcyclohexane (40 ml) was added dropwise at 15°–20° C., 14.6 ml (102.7 mmol) of iodotrimethylsilane (TMSI). The resulting slurry was agitated for 15 minutes. The silylated 7-ACA slurry was added and the mixture was agitated for 30 minutes 20° C. Iodotrimethylsilane (4.2 ml, 29.5 mmol) was added and the mixture was heated to 35° C. for 47 hours.

The product slurry was cooled to 5° C. and 2-propanol (10 ml) was added dropwise at 5°–10° C. The slurry was agitated in an ice-bath for 15 minutes. Hydriodic acid (20 ml of 57% HI in 30 ml of water) was added and the temperature was allowed to rise to 20° C. After 15 minutes agitation, the rich aqueous phase was separated. The spent solvent was extracted with water (10 ml). To the combined aqueous phase was added diatomaceous earth (3 g) and after 5 minutes agitation, activated carbon (4 g) was added. Carbon treatment was continued for 30 minutes at 20°–25° C. The carbon was removed by filtration and the spent carbon cake was washed with water (40 ml). Dilution of the filtrate with 2-propanol (500 ml) crystallized the product. The product slurry was cooled to 0°–5° C. for 1 hour, filtered and washed with 2-propanol:water (4:1) mixture (80 ml) then 2-propanol (80 ml). After drying at 45° C. in vacuo, the yield of the title compound was 16.38g (52.4%). Product purity as determined by HPLC was 95.5%.

EXAMPLE 8

7-Amino-3-[(1-methyl-1-pyrrolidinio) methyl] ceph-3-em-4-carboxylate hydriodic salt To a suspension of 7-ACA (20g, 73.5 mmol) in methylcyclohexane (140 ml) was added 18.6 ml (88.0 mmol) of hexamethyldisilazane and 0.4 ml (2.8 mmol) of iodotrimethylsilane. The suspension was heated to 50° C. and agitated under nitrogen purge for 24 hours. Methylcyclohexane (50 ml) was added and the thin suspension was heated to 50° C. in vacuo to distill out 50 ml of solvent. The silylated 7-ACA suspension was held 5.5 hours at 20°–25° C.

To a solution of N-methylpyrrolidine (NMP, 10.68 ml, 102.7 mmol) in methylcyclohexane (40 ml) was added dropwise at 15°–20° C., 14.6 ml (102.7 mmol) of iodotrimethylsilane (TMSI). The resulting suspension was agitated for 10 minutes. The silylated 7-ACA slurry was added and the mixture was agitated at 20° C. for 30 minutes.

Iodotrimethylsilane (4.2 ml, 29.5 mmol) was added and the mixture was heated to 35° C. for 40 hours. The product slurry was cooled to 5° C. and 2-propanol (10 ml) was added dropwise at 5°–10° C. The slurry was agitated in an ice-bath for 15 minutes. Hydriodic acid (20 ml of 57% HI in 30 ml of water) was added and the temperature was allowed to rise to 20° C. After 15 minutes agitation, the rich aqueous phase was separated and combined with a water (10 ml) extract of the spent solvent phase. The combined aqueous phase was treated with diatomaceous earth (3 g) for 5 minutes, then activated carbon (4 g) for 30 minutes at 20°–25° C. The carbon was removed by filtration and the spent carbon cake was washed with water (40 ml). Dilution of the filtrate with 2-propanol (500 ml) crystallized the product. The product slurry was cooled to 0°–5° C. for 2 hours, filtered and washed with 2-propanol:water (4:1) mixture (80 ml) then 2-propanol (80 ml). After drying at 45° C. in vacuo, the yield of the title compound was 16.17g (51.8%). Product purity as determined by HPLC was 97.9%.

EXAMPLE 9

7-Amino-3-[(1-methyl-1-pyrrolidinio)methyl] ceph-3-em-4-carboxylate hydriodic salt To a suspension of 7-ACA (20g, 73.5 mmol) in methylcyclopentane (140 ml) was added 18.6 ml (88.0 mmol) of hexamethyldisilazane and 0.4 ml (2.8 mmol) of iodotrimethylsilane. The suspension was heated to reflux under vacuum at 50° C. for 9 hours. The vacuum source was replaced with a nitrogen purge and the reaction was agitated at 50° C. for 10 hours. After cooling to 20° C. for 2 hours, methylcyclopentane (50 ml) was added and the reaction was heated to distill out 50 ml of solvent at 50° C. in vacuo. The thin silylated 7-ACA slurry was cooled to 20° C. for 3 hours.

To a solution of N-methylpyrrolidine (NMP, 10.68 ml, 102.7 mmol) in methylcyclopentane (40 ml) was added dropwise at 15°–20° C., 14.6 ml (102.7 mmol) of iodotrimethylsilane (TMSI). The resulting suspension was stirred at 15°–20° C. for 10 minutes. The silylated 7-ACA slurry was added and the mixture was stirred for 30 minutes at 15°–20° C. Iodotrimethylsilane (4.2 ml, 29.5 mmol) was added and the suspension was heated to 35° C. with a slight nitrogen purge for 41 hours.

The product slurry was cooled to 5° C. and 2-propanol (10 ml) was added dropwise at 5°–10° C. The slurry was agitated in an ice-bath for 15 minutes. Hydriodic acid (20 ml of 57% HI in 30 ml of water) was added and the temperature was allowed to rise to 20° C. After 15 minutes agitation, the rich aqueous phase was separated and combined with a water (10 ml) wash of the spent solvent phase. The combined aqueous phase was treated with diatomaceous earth (3 g) for 5 minutes, then activated carbon (4 g) for 30 minutes at 20°–25° C. The carbon was removed by filtration and the spent carbon cake was washed with water (40 ml). The filtrate was diluted with 2-propanol (500 ml) to crystallize the product. The product slurry was cooled to 0°–5° C. for 2 hours, filtered and washed with 2-propanol:water (4:1) mixture (80 ml) then 2-propanol (80 ml). After drying at 45° C. in vacuo, the yield of the title compound was 17.63g (56.5%). Product purity as determined by HPLC was 96.6%.

EXAMPLE 10

7-Amino-3-[(1-methyl-1-pyrrolidinio)methyl] ceph-3-em-4-carboxylate hydriodic salt To a suspension of 7-ACA (20g, 73.5 mmol) in cyclooctane (140 ml) was added 18.6 ml (88.0 mmol) of hexamethyldisilazane and 0.4 ml (2.8 mmol) of iodotrimethylsilane. The suspension was heated to reflux for 9.5 hours at 50° C. Agitation was continued at 50° C. under nitrogen purge for an additional 16 hours. The silylated 7-ACA slurry was further refluxed for 1 hour at 51° C. in vacuo then cooled to 20° C. for 3.5 hours.

To a solution of N-methylpyrrolidine (NMP, 10.68 ml, 102.7 mmol) in cyclooctane (40 ml) was added dropwise at 20°–25° C., 14.6 ml (102.7 mmol) of iodotrimethylsilane (TMSI). The slurry was stirred for 10 minutes at 20° C. The silylated 7-ACA slurry was added and agitation continued for 30 minutes at 20° C. Iodotrimethylsilane (4.2 ml, 29.5 mmol) was added and the suspension was heated to 35° C. under a slight nitrogen purge for 41 hours.

The product slurry was cooled to 5° C. and 2-propanol (10 ml) was added dropwise at 5°–10° C. The mixture was agitated in an ice-bath for 15 minutes. Hydriodic acid (20 ml of 57% HI in 30 ml of water) was added and the temperature was allowed to rise to 20° C. After 15 minutes, the rich aqueous phase was separated and combined with a water (10 ml) wash of the spent cyclooctane phase. The combined aqueous phase was treated with diatomaceous earth (3 g) for 5 minutes, then activated carbon (4 g) for 30 minutes at 20°–25° C. The carbon was removed by filtration and the spent carbon cake was washed with water (40 ml). The filtrate was diluted with 2-propanol (500 ml) to crystallize the product. The product slurry was cooled to 0°–5° C. for 1.5 hours, filtered and washed with 2-propanol:water (4:1) mixture (80 ml) then 2-propanol (80 ml). After drying at 45° C. in vacuo, the yield of the title compound was 12.11g (38.8%).

EXAMPLE 11

7-Amino-3-[(1-methyl-1-pyrrolidinio)methyl] ceph-3-em-4-carboxylate hydriodic salt To a suspension of 7-ACA (20g, 73.5 mmol) in cycloheptane (140 ml) was added 18.6 ml (88.0 mmol) of hexamethyldisilazane and 0.4 ml (2.8 mmol) of iodotrimethylsilane. The suspension was heated in vacuo to reflux for 8.5 hours at 50°–55° C. The vacuum was replaced with a nitrogen source and agitation was continued to a total of 24 hours at 50° C. Cycloheptane (50 ml) was added and at 50°–55° C. in vacuo, 50 ml of solvent was distilled out. The silylated 7-ACA suspension was cooled to 20° C. and held for 5 hours under nitrogen.

To a solution of N-methylpyrrolidine (NMP, 10.68 ml, 102.7 mmol) in cycloheptane (40 ml) was added dropwise at 25°–30° C., 14.6 ml (102.7 mmol) of iodotrimethylsilane (TMSI). The slurry was stirred for 15 minutes at 20° C. The silylated 7-ACA suspension was added and the mixture was stirred for 30 minutes at 20° C. Iodotrimethylsilane (4.2 ml, 29.5 mmol) was added and the slurry heated to 35° C. for 40 hours.

The product slurry was cooled to 5° C. and 2-propanol (10 ml) was added dropwise at 5°–10° C. The slurry was agitated in an ice-bath for 15 minutes. Hydriodic acid (20 ml of 57% HI in 30 ml of water) was added and the temperature was allowed to rise to 20° C. After 15 minutes, the rich aqueous phase was separated and combined with a water (10 ml) wash of the spent cycloheptane phase. The combined aqueous phase was treated with diatomaceous earth (3 g) for 5 minutes, then activated carbon (4 g) for 30 minutes at 20°–25° C. The carbon was removed by filtration and the spent carbon cake was washed with water (40 ml). The filtrate was diluted with 2-propanol (500 ml) to crystallize the product. The product slurry was cooled to 5° C. for 1 hour, filtered and washed with 2-propanol:water (4:1) mixture (80 ml) then 2-propanol (80 ml). After drying at 45° C. in vacuo, the yield of the title compound was 14.54g (46.6%). Product purity as determined by HPLC was 96.2%.

EXAMPLE 12

7-Amino-3-[(1-methyl-1-pyrrolidinio)methyl] ceph-3-em-4-carboxylate hydriodic salt To a suspension of 7-ACA (20g, 73.5 mmol) in 1,3 dimethylcyclohexane at 20° C. was added 18.6 ml (88.0 mmol) of hexamethyldisilazane and 0.4 ml (2.8 mmol) of iodotrimethylsilane. The suspension was agitated at 50° C. under a slight nitrogen purge for 21 hours. Fresh 1,3 dimethylcyclohexane (50 ml) was added and, in vacuo at 50° C., 50 ml of solvent was distilled off. The thin slurry was held at 20°–25° C. for 3 hours.

To a solution of N-methylpyrrolidine (NMP, 10.68 ml, 102.7 mmol) in 1,3 dimethylcyclohexane (40 ml) was added dropwise at 20° C., 14.6 ml (102.7 mmol) of iodotrimethylsilane (TMSI). The slurry was stirred for 10 minutes at 20° C. and the silylated 7-ACA was added. After 30 minutes at 20°–25° C., iodotrimethylsilane (4.2 ml, 29.5 mmol) was added. The slurry was heated to 35° C. for 44 hours under a slight nitrogen purge.

The product slurry was cooled to 7° C. and 2-propanol (10 ml) was added dropwise at 7°–10° C. The slurry was agitated in an ice-bath for 15 minutes. Hydriodic acid (20 ml of 57% HI in 30 ml of water) was added and the temperature was allowed to rise to 20° C. After 15 minutes, the rich aqueous phase was separated and combined with a water (10 ml) wash of the spent solvent phase. The combined aqueous phase was treated with diatomaceous earth (3 g) for 5 minutes, then activated carbon (4 g) for an additional 30 minutes. The carbon was removed by filtration and the spent carbon cake was washed with water (40 ml). The filtrate was diluted with 2-propanol (500 ml) to crystallize the product. The product slurry was stirred at 0°–5° C. for 2 hours, filtered and washed with 2-propanol:water (4:1) mixture (80 ml) then 2-propanol (80 ml). After drying at 45° C. in vacuo, the yield of the title compound was 13.33g (42.7%). Product purity as determined by HPLC was 91%.

What is claimed is:

1. A process for the preparation of a stable, crystalline compound having the Formula I

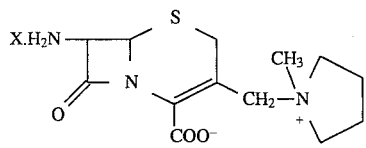

wherein X is HI, HCl or $H_2SO_4$ which is substantially free of the $\Delta^2$ isomer, which comprises treating the compound of Formula II

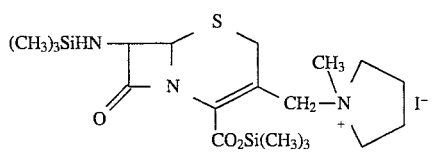

in a $C_{5-8}$ cycloalkane optionally substituted by one or two (lower)alkyl with a (lower)alkanol to remove the silyl groups, followed by acidification to produce a compound of Formula I.

2. A process of claim 1 further comprising the preparation of a compound of Formula II which is substantially free of the $\Delta^2$ isomer by reacting the compound of Formula III

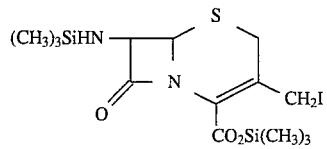

with a compound of the formula

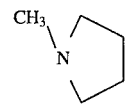

in a $C_{5-8}$ cycloalkane optionally substituted by one or two (lower)alkyl.

3. A process of claim 2 further comprising the preparation of a compound of Formula III which is substantially free of the $\Delta^2$ isomer by treating the compound of Formula IV

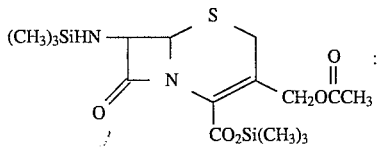

in a $C_{5-8}$ cycloalkane optionally substituted by one or two (lower)alkyl with at least one equivalent of iodotrimethylsilane per equivalent of compound IV.

4. A process of claim 3 further comprising the preparation of a compound of Formula IV which is substantially free of the $\Delta^2$ isomer by treating the compound of Formula V

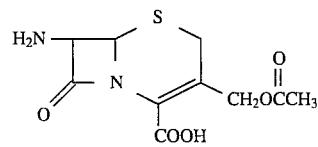

in a $C_{5-8}$ cycloalkane optionally substituted by one or two (lower)alkyl with at least one equivalent of hexamethyldisilazane per equivalent of compound V and a catalytic amount of iodotrimethylsilane.

5. A process for the preparation of a stable, crystalline compound of the Formula I

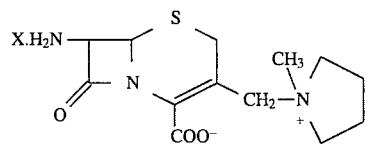

wherein X is HI, HCl or $H_2SO_4$ which is substantially free of the $\Delta^2$ isomer, which comprises treating a solution of the compound of Formula IV

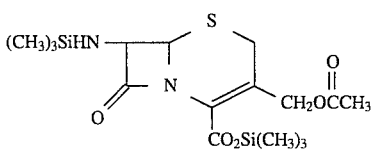

in a $C_{5-8}$ cycloalkane optionally substituted by one or two (lower)alkyl with at least one equivalent of a compound of the formula

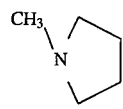

then with at least one equivalent of iodotrimethylsilane per equivalent of compound IV followed by treatment with a (lower)alkanol to remove the silyl groups, and acidification to produce a compound of Formula I.

6. A process for the preparation of a stable, crystalline compound of the Formula I

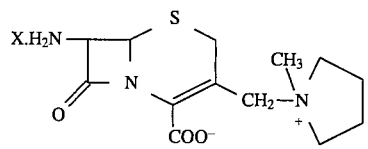

wherein X is HI, HCl or $H_2SO_4$ which is substantially free of the $\Delta^2$ isomer, which comprises treating the compound of Formula IV

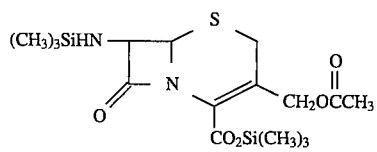

in a $C_{5-8}$ cycloalkane optionally substituted by one or two (lower)alkyl with a compound of formula

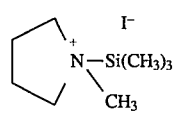

in a $C_{5-8}$ cycloalkane optionally substituted by one or two (lower)alkyl, followed by treatment with a (lower)alkanol to remove the silyl groups, and acidification to produce a compound of Formula I.

7. A process of claim 6 further comprising the preparation of a compound of Formula IV which is substantially free of the $\Delta^2$ isomer by treating the compound of Formula V

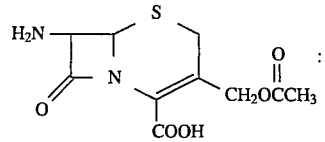

in a $C_{5-8}$ cycloalkane optionally substituted by one or two (lower)alkyl with at least one equivalent of hexamethyldisilazane per equivalent of compound V and a catalytic amount of iodotrimethylsilane.

8. A process of claim 1, 5 or 6 wherein the (lower)alkanol is methanol or 2-propanol.

9. A process of claim 1, 5 or 6 wherein the $C_{5-8}$ cycloalkane is cyclopentane or cyclohexane.

10. A process of claim 1, 5 or 6 wherein the $C_{5-8}$ cycloalkane is methylcyclopentane or methylcyclohexane.

* * * * *